(12) United States Patent
Heldens et al.

(10) Patent No.: US 9,157,093 B2
(45) Date of Patent: Oct. 13, 2015

(54) PROMOTOR SEQUENCE AND GENE CONSTRUCT FOR INCREASING CROP YIELD IN TOMATO

(75) Inventors: Jozef Wilhelmus Gerardus Heldens, Enkhuizen (NL); Marieke Ykema, Harlingen (NL); Frits Herlaar, Westwoud (NL); Martyn Petrus Van Stee, Lelystad (NL); Johannes Jacobus Maria Lambalk, Middenbeemster (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 1429 days.

(21) Appl. No.: 12/672,846

(22) PCT Filed: Aug. 10, 2007

(86) PCT No.: PCT/EP2007/058309
§ 371 (c)(1),
(2), (4) Date: Nov. 30, 2011

(87) PCT Pub. No.: WO2009/021545
PCT Pub. Date: Feb. 19, 2009

(65) Prior Publication Data
US 2010/0212046 A1    Aug. 19, 2010

(51) Int. Cl.
*C12N 15/82* (2006.01)
*C12N 15/87* (2006.01)

(52) U.S. Cl.
CPC .......... *C12N 15/827* (2013.01); *C12N 15/8222* (2013.01); *C12N 15/8242* (2013.01)

(58) Field of Classification Search
CPC ............. C12N 15/827; C12N 15/8222; C12N 15/8242
USPC ....................................... 536/24.1
See application file for complete search history.

(56) References Cited

U.S. PATENT DOCUMENTS 6,100,449 A * 8/2000 Fluhr et al. ..................... 800/279

OTHER PUBLICATIONS

Carmel-Goren et al. 2003 Plant Mol. Biol. 52 (6), 1215-1222.*
Molinero-Rosales et al., "Single Flower Truss regulates the transition and maintenance of flowering in tomato," *Planta.* 218(3):427-434 (2004).
Carmel-Goren et al., "The Self-Pruning gene family in tomato," *Plant Mol. Biol.* 52(6):1215-1222 (2003).
Lifschitz et al., "The tomato FT ortholog triggers systemic signals that regulate growth and flowering and substitute for diverse environmental stimuli," *Proc. Natl. Acad. Sci. USA.* 103(16):6398-6403 (2006).
Database EMBL *lycopersicon* esculentum SP3D gene. Carmel-Goren et al. (2003).

* cited by examiner

*Primary Examiner* — Li Zheng
(74) *Attorney, Agent, or Firm* — The Webb Law Firm

(57) ABSTRACT

Presented herein is a SP3D promotor sequence, capable of directing transcription of a downstream SP3D gene that is operably linked to said promotor sequence, wherein the promotor sequence is derived from a species of the Solanaceae family having a sympodial index of 2, for reducing sympodial index in plants having a sympodial index of 3 or more. Also presented herein are methods for providing plants of the Solanaceae family, in particular *S. lycopersicum*, having a reduced sympodial index including the steps of introducing into the genome of said plants a promotor sequence in operable linkage with a downstream SP3D gene, or introducing into said plants a gene construct, such that the sympodial index of the plant with the promotor sequence or gene construct is reduced as compared to the plant without said promotor sequence or gene construct, and to plants obtainable by said methods.

17 Claims, 9 Drawing Sheets

FIG. 1

| primer sequence | primer naam |
|---|---|
| AGG AGT ACT CTT GTG TTG TGT TTT TG | dSP3D f1 |
| AAC AAG AGG ATC GCG TTC TCT A | dSP3D r1 |
| GGA CGT ATG CGA TGT ATC GGG AT | sp3d 10fa |
| CCC ACA CTA CGC CAA AAG TT | SP3D f2 |
| AGT AGA TGG AGT TGA TCA ATC AGC A | SP3D R |

FIG. 2-1

ACCATGATTACGAATTCGAGCTCGGTACCCGGGGATCACCCTCTATTAGGACTCGTAAAA
AGTTCTGAGGATACACAATACATTTAAATTAATTTTCTTAAGCATTCAATAATACATTTA
TTTTGTTTTTACATCTTTATATGACGTTACTGATCTCAGAGCTAGGGCTAAAGCTCTCGG
GCTTATAGTTACAAGCACTATGAAAACATCCAAACTTTTGACTCTTCTACTATTAAACAA
CTTTATTTCATTATATTCACTTTTGTCCTTGCTAATAAATCAAACCTTTAGTAAACGAAT
ATAAAAAGAACCAAGTAAAGACATGTGCTGTTGTCCTCCTACAAATTCAACCCAACCTAT
TTTAGGGTAAACAAATTCGGAAAACATTACTGGTGAATTTCTGACACCTTTCGTAAATTA
AAATATATTTATTCAAACTCATAAATTTAAAATTATAAATTCGCGTTAGGAAGGAATGCT
AAGAAATAGAATGAGTCGAAAGAGTTTCAAAGAAGGAGAGAACCAATGTCATTATCAGAC
TGAAATGTATGTCAAACAGATACAATGTATGGTAATGATAGAACTAATTAACTACATACC
ACTAATTGCACTATATTATCAGCTACCCACCTAACTAACTTCTATCAAAATTAACTGTTA
AACCAACAATTTAACTTACTCCTCTTTTCATATTACTTTGATCTCTATTGATCTAGTATA
TCATTTTAGAAAACTTTAATTATATGTGTATATTAATCTAATCTCGTTAGCAATGTTTTG
GAACTATGACTATTAGTTTAAGTTGTTATTTAATACTAAAGGTAGAAAAAGAAAAATATA
GCAAAATTTTCTTATTTTCATAAATTAGGTTAGCAAGTAATTATTTTTAGTACGAAGATA
AAAGTAATATTAAAGGAGGGAGTAACCAATATGTAGCTATATGTCATAGTCAACAAATCA
GTAGCATGGATTTCTAAGACTACCAACTTAAAGAATAAGACACGGGTGATAATTTAAACC
AGTTTAGGTAGGGGTAAGGGTAAAATATTGGAAAAACTATTTAAATATATAACTTATTTT
ATTATAATTTTTAAAATTTTCTACTATTTGAAAAAAAAAATATAACAAATACTACTTTACG
TGATGTATCAGTCAAATACATCACTTTATACTATATATCGTTCAGATACATCACTTTATG
CGATATATAGTTGTATACATCACTTTACGCGTTGTAATCTGAACGTATGCGATGTATCGG
GATATTGTTACTTTACGTGATGTATCGGTCGAACATACATTACTTTACGCGATGCAGAAC
GTTGAGAGATGTATCCAAAATCAAGACACGATGATATTGAGACGTTTTGGGGTTTATTCG
AATTTCACCAAATTTAAGAAATTTTTGTAATTTGAAAAAGAGTCCGTTGATTCATAACAT
AATGAAATTTGTGTAAAATCATGAAAAATATTTTAACACAAATTGCTATGTAGAAGTAAT
TTCCACAAAAAAAAAAGAATTTCTAATCCGCAGCCGCTACCCTTTGGCTTTTCCTTTGT
CAAAAAATAAAATGAAAACTAATCTTCAAATATGACATGATTCGATTAGAAGAATTCCTA
GAAAACCTATGGTTGTAAGGTGGGAAAAGAGAAGTAATTAAAAAAGGCACGTACTAGATT
CTTTAGGAGGATATGACAGCAAAGGTGCTAGCATGTGTATATATACACACATTCTACCT
CTACACTTGTAAAAATATGCATAGCCCGATAAGAAACTAGCTAGCTAGGAGTACTCTTGT
GTTGTGTTTTACCACACAAATACACAAAAGTTAGCCATAGCTAGTTTTTATTTTGTTTAT
CGTCAACCATCGTCATGCCTAGAGAACGCGATCCTCTTGTTGTTGGTCGTGTGGTAGGGG
ATGTATTGGACCCTTTCACAAGAACTATTGGCCTAAGAGTTATATATAGAGATAGAGAAG
TTAATAATGGATGtGAGCTTAGGCCTTCCCAAGTTATTAACCAGCCAAGGGTTGAAGTTG
GAGGAGATGACCTACGTACCTTTTTCACTTTGGTAATATTTCTTATATTTTTGTTTGGG
AATATAATTAAGTTATTATTTCTATGATTTTCATAAGCAAAGTAAAAAGTATTTTTGTCT
TTTTGTAAAGGTTATGGTGGACCCTGATGCTCCAAGTCCGAGTGATCCAAATCTGAGAGA
ATACCTTCACTGGTCCGTATTTTCCTTATTCTCTCTTCTTTTAATCTCTTTCTTTTTT
GACCTTTTCACTTTCCCATAATAATTATATTCTTTAGTAATTATATATCCTTTTATTTTA
TTTTTAAAAATTGGAAAGGAGAAACGAAGAGGAGATTTTTACATGTGAGGGATTTAATTG
TAATGCAAATGGTAGAAATATATAAATGTGAAGATATATTCTTGAACTTAAAAACAAACT
ACTAAAATAAAATGAATAAAATATTTACTCTGTCAATATTCTGTACTATATTGGTCAAT
GAATATTTATATTATTCATGACTTTAAAAATAGTCAAACCGAGACATAAGGTAAAAGTCA
AAATACGTTTAAGCTCATTCATATAAATGAATATTTTTAAATTTTGTTGCATCCATCAAA
ATATCTACTTTTTAAGAATGATATTTATTTTATAATATTCATATTTGATTCGTTGATGGA
TAGATTTTATTCTGTAAGAAATTAAATAAAAATAAAAATTTAGGCCTAGTCATATCCATC
TAAAATGGGTGAGATTCTGGTACGCTGACCGTCTTATAATTCCCAATAAAAACTTTTGGA

FIG. 2-2

AAAAAAGGGTACAGAAAATAGTGCACCAATAGAATCACTTCTCACCTCTTTATAGCTAGT
ACGGATTATTCCCTTCATGTGTGCCACAGTCATGAACAATCCATATTATAATTTCGGACA
TAATTAATTGTTCATATATCTATTAACATAATAAATTTACCATTTATTCTTTTTACTTAT
AAAGTAGATACATTAAAAAATTTAAGATTTCCAGAAAGTTCTACATTTTTCAAAATAATC
AATTGAGGGTATAAAAAAGTTGTCCTTCCTTAATTTCTCAAGATGAATAAGTAATTAAGA
ACAATTAAAAAAAGCGAACAAATGAATATTTATCAATCCTCATTTCACCAAGTCATTAAA
TTATTTTATGACCTAAATGTTTACTCATTTTGCTTAAATATCAAGAAAATTGTTGAATTA
TCTCTTATAGAAATATCACTCAACATCAATATCTAATTAGTACTCATTTCGTTTTTATTT
ATATGTCGTTTTTATTAAAAATAGATGTTTTTTAATATTTATCATTTTACAAAATCAAA
ATTTGACTTATGATTACTAAATAATTAATTCAATTAATTAATCAAAATAAATTAATTTA
TCTCTTATTTAAAAGTTGACTTTAAGAAAACACCAATTAAAAATATAATAATAAACTTAG
CTAGTTTTTTAAAAGATATAAAATCTAAATCAGTGACATATAAATAGAAACAGAGGGGAA
AGTAGTAGTTTAACTCTTATGGTTTGTTAAGGTGCGTGCTAAATGACAACATCTTTCTTG
TCTTGTAAAGTTAACATCTTAGTAGGTGGTGAGTAAGTGAGTGAATGCCATTGAATGAAG
AGATTATTTGTTTTTGTCACCTTTACCACTAAAGTTTTGTCTATTTTTATTCTTTGAATT
CCTCCTGTACAAGATTTTATTTTGATATTCCTTTCTTTTGGAATTCAGAGTTGGTATAA
ACAGGATCTATTTGGCTATCACACATATATTTTAAACAAAAATCAATATTTAGACATTT
AGTTCACATTTCATGGATTATACTCGTTAGAAAAGTATATTTAAGCAATTAAATATTAT
TTGTTAAACATAGAAAATGATTTGAAATATATTCAAACTTTGATCACAATTGTGGTAAC
AATTTCAAATCTTGGGAAGGACCTTTTATTTCCCTTGCGCTATTTATAGTGTATTTAAA
TGTATATATATGTCAACATAAATATCATAAATATTACATTATTATATATAGTAACTTGTT
CACGTGGACACATGTATACCTGTAAAATATACTATTAAATAGTATAGGAGATAGTAGGTC
CTGCTCAAAGTTAGAGATTGTTATAGCAATTTCGATCAAAGATATATTTCGAACTATTTT
TCCTAAAAGATATAACCAAATACAATTTTATCTTTAATTTCAAAATTTGCAAATAAAGTG
AAAAAAATATTTATACCAAGTAGGATGAATTAAAAATTAAGGGTTTTTTTTCCTTGTCTA
TTTCTTCTTGTTATATATGACTAATCATCATTTTTTATTAATGAATCGTCGGCAG<u>*GT*</u>
<u>*TGGTCACtGATATTCCAGCTACCACAGGTTCAAGTTTTG*</u>GTGAGAATCCTCTTTTTGTTA
ATTGTTTGTTTGTTGTCTTCCCATGTTTACATTTTTTTAAAAAAAAAAACTAATTTTAA
AGGTAGAATAAAAAAAAAATCATTATCGCATTTAAAAATATATGTTTATAATAACATAGA
CGAATAATATGAAACTAACGGAGTAATGACAAAGGAATTTATACTGAGCGGGCAATGTTG
CGTTAAATCATGTTGGTCCTAAACTTTTAAAACCTAGGAAAGGGAATGAAATCTATTCTC
AATTAACGTGATTAAATATTCTAAACAATTGATATCCTTTAATTATGTCCCACACTACTC
CAAAAGTTCTTAAGCACTACACTCTAAAATTTGTATACATAACATTAAAAGATCATTACC
TATTTGGCTAAATTTTTACAATAAGTTTATTTTAAAAAGTGTTCCTTTTTTTTTCCTCTC
AAAAACACACTTGTGTTTCTCTTGATTTTTCTCTCAAAAGTTTAGTTAAATACTTAGTTT
TTTTCAAATAATTTTTTTATGAAAAAGAAAAAAAAACATTTTTGGCTAACCAAACAGGT
TTAGGAGATTTGCGCTCTGCCATAAGTATTTCCCCATTCACTTTTCTTCCATTTTTATTT
ATGATTTTTTTTAACATATTAAGAAAGATATTTGTTTCATGCTCTTCATTAATTTCTTAT
CCTCCAAATTAACATAGATATTGTGGTAAAACACCATAATAGTTATTGTATATTTGTATA
CCTTTTCAAATGTATATACTCTCTAATCCTTTGTTTCCTTGGTTTAAGATCACAAGAT
AGATAAAAAAACATTTATTGGTGAATAAATTTGACATAACTTTAATTTAATTATGACACG
AAATTCAAAAGTTTTATTTCTTAACTTAAAAATTTGGTGTCAAGTCAGAAGTAGATGTGA
TAATTTTGTTTTTGAAATTGGAGGGAGTATCTTGTTGAAAATATTGGATATGTACATAAG
AAGTAGTCATTTGAAATGCATGGAAACTTGATAAAAACATAAGTAGCTAGCTAGTGCATG
AAAGTTTGGTTGTTTATGTTCTTTTAATATGTAG<u>*GGCAAGAAATAGTGAGCTATGAAAGT*</u>
<u>*CCAAGACCATCAATGGGAATACATCGATTTGTATTTGTATTATTCAGACAATTAGGTCGa*</u>
<u>*CAAACAGTGTATGCTCCAGGATGGCGTCAGAATTTCAACACAAGAGATTTTGCAGAACTT*</u>
<u>*TATAATCTTGGTTTACCTGTTGCTGCTGTCTATTTTAATTGTCAAAGAGAGAGTGGCAGT*</u>
<u>*GGTGGACGTAGAAGATCTGCTGATTGA*</u>TCAACTCCATCTACTACAAAAAAAAAAAAAAA

FIG. 2-3

```
AACAATGCATCCCTCCCCCTTTTTATATTTTTAGCTAATAATAACCACCAATATCTACTA
TCACTACTACTTTTCTTACAACTTTAGTAGTATCTATATATATCTTTTTTAATCTACTCT
TTTACTTCTTTACTATATTGTCTTCCACACTACTATACACTACTATTGCTATTATCTTTC
GTCTCAATTTATTTGAATTAGTGACTTGATACCAAGTTTCAAGAAAGAAATAAAGACTGA
CTTTTGAATTTTGTGATTTACAATAAGTTGTACATATTTGTATGACTATTTTAAAAGTTT
AAATTATTATTAAATATAATTAATTTAAAAGGAAGTAAATTATATAACATGTTAATTAAT
TTTTTTTAATTTAGCTTTTAAAAAGAAAGAAAATTAACACAATTAAAAGTATTGAATGA
AAGAAGTTTGTACCTAGTTTCTGTTATTCCTCTATAAAACAGTATATTTTCTTGTTACTT
TTATAAATTTCTAAGATATGAACTTCCTTGACTTTTAAGTAGTATTATTTAGCATAAAAC
AAGTTCCAATAAGGAATCTTGAGTGGAAGTACTTGTAGGGCAGTAAAAGGGCCGCCTCTT
TGTCACCAAACCAGTTGAGTTTGCTTTGGAAATACAACAGTCGTCATCCAACTTCCTTTT
CCACAAAGCCTTAACAGTGGATATTAATGTACAAACTTACCTTCGTTCAAATGACGTACA
TAATTACATTTACATTCCATCATGAAAAATTTGCTTCGTCTATCTTTAATTGTCATGATT
TCTATTATTATAAAATTTTAATTAACATTTTAATATGTATATATTCATCATATTGATAA
GTAAAAAATTACAAGTTATAGTACTTTTCATAGAGTTTTTGTATATCTGTTTTTTTTTAA
AAATATCAAATTAATAATAACTAATTCAACTTTAAAAATTAGTTTAATTAATTTCGAAAA
ACGCAAATAACAAATAAAAATGGAAAAGTAGATAATATAAAATTAAAATAATAAAATCTG
ATTAAAACTATAGTCTAATTTATATAAAGGAACCCTAAGAATCTTCTAACTTATCCATTA
CAAAAGGATGTAATTTATGGAGTTAACAGACGTGTATATAGATAGACTTGAAAGTAAAAG
AAAACTTTAACTCTAGGAACTTCTCTATAAATACGGTTGCTAGGAGCTCCTAATAAAATG
TGTCTCCATCCATCAAGCAAACTACCTACAAGATATGCATAACTTTCGCGATTCGATTCC
TCGAGTCATGATAACTTCTATTATAATTCATCAAAGGATAAATTAACCCGTATATCTAGA
ACAACAAATAATTAGTACAAGAACTAAACAGAAAATAATACTAACAGAAGAAGAAGACAA
AAACAAGATCAAACCAAAACTATATATATATATAAAATAGAAATCCTCCAAAAACCTGAA
AGTCACGAGTAAAAAACTATCTAGTAAAAATAAATACAAGTGATAAAAGTGGACCATAAC
AAGTCATCTCAAGGGCAAAAGACTAGAGTCGACCTGCAGGCTGCAGC
//
```

FIG. 4

| | | | | ↓ | | |
|---|---|---|---|---|---|---|
| LYC00009 S. esculentum | TCTT | GTGTTGTGTT | TTAGCTCACA | AATACACAAA | AG | |
| LYC00118 S. pimpinellifoll... | TCTT | GTGTTCGGTT | TTAGCTCACA | AATACACAAA | AG | |
| LYC00034 S. pimpinellifoll... | TCTT | CGCGTGTGTT | TTAGCTCACA | AATACACAAA | AG | |
| LYC00189 S. pimpinellifoll... | TCTT | GTGTTGTGTT | TTAGCTCACA | AATACACAAA | AG | |
| LYC00122 S. cheesmanii | TCTT | GKGTTCGGTT | TTAGCTCACA | AATACACAAA | AG | |
| LYC00170 S. cheesmanii | TCTT | GTGTTCKGTT | TTAGCTCACA | AATACACAAA | AG | |
| LYC00053 S. cheesmanii | TCTT | GTGTTGTGTT | TTAGCTCACA | AATACACAAA | AG | |
| LYC00156 S. cheesmanii | TCTT | GTGTTGTGTT | TTAGCTCACA | AATACACAAA | AG | |
| LYC00114 S. cheesmanii | TCTT | GTGTTGTGTT | TTAGCTCACA | AATACACAAA | AG | |
| LYC00152 S. cheesmanii | TCTT | GTGTTGTGTT | TTAGCTCACA | AATACACAAA | AG | Spi=3 |
| LYC00154 S. cheesmanii | TCTT | GTGTTGTGTT | TTAGCTCACA | AATACACAAA | AG | |
| LYC00158 S. cheesmanii | TCTT | GTGTTGTGTT | TTAGCTCACA | AATACACAAA | AG | |
| LYC00159 S. cheesmanii | TCTT | GTGTTGTGTT | TTAGCTCACA | AATACACAAA | AG | |
| LYC00176 S. cheesmanii | TCTT | GTGTTGTGTT | TTAGCTCACA | AATACACAAA | AG | |
| LYC00153 S. cheesmanii | TCTT | GTGTTGTGTT | TTAGCTCACA | AATACACAAA | AG | |
| LYC00016 S. habrochaites | TCTT | GTGTTGTGTT | TTAGTACACA | AATACACAAA | AG | |
| LYC00032 S. habrochaites | TCTT | GTGTTGTGTT | TTAGTACACA | AATACACAAA | AG | |
| LYC00217 S. habrochaites | TCTT | GTGTTGTGTT | TTAGTACACA | AATACACAAA | AG | |
| LYC00040 S. habrochaites | TCTT | GTGTTGTGTT | TTAGTACACA | AATACACAAA | AG | |
| LYC00211 S. habrochaites | TCTT | GTGTTGTGTT | TTAGTACACA | AATACACAAA | AG | |
| LYC00213 S. habrochaites | TCTT | GTGTTGTGTT | TTAGTACACA | AATACACAAA | AG | |
| LYC00216 S. habrochaites | TCTT | GTGTTGTGTT | TTAGTACACA | AATACACAAA | AG | |
| LYC00215 S. pennellii | TCTT | GTGTTGTGTT | TTAGCACACA | AATACACAAA | AG | |
| LYC00137 S. parviflorum | TCTT | GTGTTGTGTT | TTAGCACACA | AATACACAAA | AG | |
| LYC00142 S. peruvianum | TCTT | GTGTTGTGTT | TTAGCACACA | AATACACAAA | AG | |
| LYC00171 S. peruvianum | TCTT | GTGTTGTGTT | TTAGCACACA | AATACACAAA | AG | |
| LYC00048 S. peruvianum | TCTT | GTGTTGTGTT | TTAGCACACA | AATACAGAAA | AG | |
| LYC00111 S. peruvianum | TCTT | GTGTTGTGTT | TTAGCACACA | AATACACAAA | AG | |
| LYC00120 S. peruvianum | TCTT | GTGTTGTGTT | TTAGCACACA | AATACACAAA | AG | |
| LYC00049 S. peruvianum | TCTT | GTGTTGTGTT | TTAGCACACA | AATACACAAA | AG | |
| LYC00143 S. peruvianum | TCTT | GTGTTGTGTT | TTAGCACACA | AATACACAAA | AG | |
| LYC00136 S. parviflorum | TCTT | GTGTTGTGTT | TTAGCACACA | AATACACAAA | AG | |
| LYC00127 S. parviflorum | TCTT | GTGTTGTGTT | TTAGCACACA | AATACACAAA | AG | |
| LYC00128 S. parviflorum | TCTT | GTGTTGTGTT | TTAGCACACA | AATACACAAA | AG | |
| LYC00131 S. parviflorum | TCTT | GTGTTGTGTT | TTAGCACACA | AATACACAAA | AG | |
| LYC00132 S. parviflorum | TCTT | GTGTTGTGTT | TTAGCACATA | AATACACAAA | AG | Spi=2 |
| LYC00133 S. parviflorum | TCTT | GTGTTGTGTT | TTAGCACACA | AATACACAAA | AG | |
| LYC00134 S. parviflorum | TCTT | GTGTTGTGTT | TTAGCACACA | AATACACAAA | AG | |
| LYC00135 S. parviflorum | TCTT | GTGTTGTGTT | TTAGCACATA | AATACACAAA | AG | |
| LYC00138 S. parviflorum | TCTT | GTGTTGTGTT | TTAGCACACA | AATACACAAA | AG | |
| LYC00148 S.chmielewskii | TCTT | GTGTTGTGTT | TTAGCACACA | AATACACAAA | AG | |
| LYC00081 S.chmielewskii | TCTT | GTGTTGTGTT | TTAGCACACA | AATACACAAA | AG | |
| LYC00121 S.chmielewskii | TCTT | GTGTTGTGTT | TTAGCACACA | AATACACAAA | AG | |
| LYC00150 S.chmielewskii | TCTT | GTGTTGTGTT | TTAGCACACA | AATACACAAA | AG | |
| LYC00141 S.chmielewskii | TCTT | GTGTTGTGTT | TTAGCACACA | AATACACAAA | AG | |
| LYC00144 S.chmielewskii | TCTT | GTGTTGTGTT | TTAGCACACA | AATACACAAA | AG | |
| LYC00146 S.chmielewskii | TCTT | GTGTTGTGTT | TTAGCACACA | AATACACAAA | AG | |
| LYC00149 S.chmielewskii | TCTT | GTGTTGTGTT | TTAGCACACA | AATACACAAA | AG | |
| LYC00162 S.chmielewskii | TCTT | GTGTTGTGTT | TTAGCACACA | AATACACAAA | AG | |
| LYC00173 S.chmielewskii | TCTT | GTGTTGTGTT | TTAGCACACA | AATACACAAA | AG | |
| LYC00174 S.chmielewskii | TCTT | GTGTTGTGTT | TTAGCACACA | AATACACAAA | AG | |
| LYC00180 S. chilense | TCTT | GTGTTGTGTT | TTAGCACACA | AATACACAAA | AG | |
| LYC00074 S. chilense | TCTT | GTGTTGTGTT | TTAGCACACA | AATACACAAA | AG | |

FIG. 7

| master field | genotype | SPI | #leaves 1 truss | #fruit | Fruit weight (gr) | # trusses | Total KG | Fruits/ truss |
|---|---|---|---|---|---|---|---|---|
| 15751 | SP3Dpen/SP3Dpen | 2,4 | 5.8 | 107 | 57 | 14 | 6,0 | 7,6 |
| 15753 | SP3Dpen/SP3Desc | 2,5 | 5.8 | 92 | 56 | 14 | 5.0 | 6.6 |
| 15769 | SP3Desc/SP3Desc | 2,7 | 7.5 | 60 | 59 | 9 | 3,5 | 6,7 |

SEQUENCE LISTING

```
<160> NUMBER OF SEQ ID NOS: 63

<210> SEQ ID NO 1
<211> LENGTH: 25
<212> TYPE: DNA
<213> ORGANISM: Lycopersicon pennellii

<400> SEQUENCE: 1
aggagtactc ttgtgttgtg ttttg                                        25

<210> SEQ ID NO 2
<211> LENGTH: 22
<212> TYPE: DNA
<213> ORGANISM: Lycopersicon pennellii

<400> SEQUENCE: 2
aacaagagga tcgcgttctc ta                                           22

<210> SEQ ID NO 3
<211> LENGTH: 23
<212> TYPE: DNA
<213> ORGANISM: Lycopersicon pennellii

<400> SEQUENCE: 3
ggacgtatgc gatgtatcgg gat                                          23

<210> SEQ ID NO 4
<211> LENGTH: 20
<212> TYPE: DNA
<213> ORGANISM: Lycopersicon pennellii

<400> SEQUENCE: 4
cccacactac gccaaaagtt                                              20

<210> SEQ ID NO 5
<211> LENGTH: 25
<212> TYPE: DNA
<213> ORGANISM: Lycopersicon pennellii
```

-continued

```
<400> SEQUENCE: 5
agtagatgga gttgatcaat cagca                                           25

<210> SEQ ID NO 6
<211> LENGTH: 7307
<212> TYPE: DNA
<213> ORGANISM: Lycopersicon pennellii

<400> SEQUENCE: 6
accatgatta cgaattcgag ctcggtaccc ggggatcacc ctctattagg actcgtaaaa     60
agttctgagg atacacaata catttaaatt aattttctta agcattcaat aatacattta    120
ttttgttttt acatctttat atgacgttac tgatctcaga gctagggcta aagctctcgg    180
gcttatagtt acaagcacta tgaaaacatc caaacttttg actcttctac tattaaacaa    240
ctttatttca ttatattcac ttttgtcctt gctaataaat caaacccttta gtaaacgaat    300 ataaaaagaa ccaagtaaag acatgtgctg ttgtcctcct acaaattcaa cccaacctat    360
tttagggtaa acaaattcgg aaaacattac tggtgaattt ctgacacctt tcgtaaatta    420
aaatatattt attcaaactc ataaatttaa aattataaat tcgcgttagg aaggaatgct    480
aagaaataga atgagtcgaa agagtttcaa agaaggagag aaccaatgtc attatcagac    540
tgaaatgtat gtcaaacaga tacaatgtat ggtaatgata gaactaatta actacatacc    600
actaattgca ctatattatc agctacccac ctaactaact tctatcaaaa ttaactgtta    660
aaccaacaat ttaacttact cctcttttca tattactttg atctctattg atctagtata    720 tcatttttaga aaacttttaat tatatgtgta tattaatcta atctcgttag caatgttttg    780
gaactatgac tattagttta agttgttatt taatactaaa ggtagaaaaa gaaaaatata    840
gcaaaatttt cttattttca taaattaggt tagcaagtaa ttatttttag tacgaagata    900
aaagtaatat taaaggaggg agtaaccaat atgtagctat atgtcatagt caacaaatca    960
gtagcatgga tttctaagac taccaactta aagaataaga cacgggtgat aatttaaacc   1020
agtttaggta ggggtaaggg taaaatattg gaaaaactat ttaaatatat aacttatttt   1080
attataattt ttaaaatttt ctactatttg aaaaaaaaat ataacaaata ctactttacg   1140
tgatgtatca gtcaaataca tcactttata ctatatatcg ttcagataca tcactttatg   1200
cgatatatag ttgtatacat cactttacgc gttgtaatct gaacgtatgc gatgtatcgg   1260
gatattgtta ctttacgtga tgtatcggtc gaacatacat tactttacgc gatgcagaac   1320
gttgagagat gtatccaaaa tcaagacacg atgatattga gacgttttgg ggtttattcg   1380
aatttcacca aatttaagaa attttttgtaa tttgaaaaag agtccgttga ttcataacat   1440
aatgaaattt gtgtaaaatc atgaaaaata ttttaacaca aattgctatg tagaagtaat   1500
ttccacaaaa aaaaaagaa tttctaatcc gcagccgcta ccctttggct tttccttttgt   1560 caaaaaataa aatgaaaact aatcttcaaa tatgacatga ttcgattaga agaattccta   1620
gaaaacctat ggttgtaagg tgggaaaaga gaagtaatta aaaaaggcac gtactagatt   1680
ctttaggagg atatgacagc aaaaggtgct agcatgtgta tatatacaca cattctacct   1740
ctacacttgt aaaatatgc atagcccgat aagaaactag ctagctagga gtactcttgt   1800
gttgtgtttt agcacacaaa tacacaaaag ttagccatag ctagtttttta ttttgtttat   1860 cgtcaaccat cgtcatgcct agagaacgcg atcctcttgt tgttggtcgt gtggtagggg   1920
atgtattgga ccctttcaca agaactattg gcctaagagt tatatataga gatagagaag   1980
ttaataatgg atgtgagctt aggccttccc aagttattaa ccagccaagg gttgaagttg   2040
```

```
gaggagatga cctacgtacc tttttcactt tggtaatatt tcttatattt tttgtttggg    2100
aatataatta agttattatt tctatgattt tcataagcaa agtaaaaagt atttttgtct    2160
ttttgtaaag gttatggtgg accctgatgc tccaagtccg agtgatccaa atctgagaga    2220
ataccttcac tggtccgtat ttttccttat tctctcttct ttttaatctc tttctttttt    2280 gacctttca ctttcccata ataattatat tctttagtaa ttatatatcc ttttatttta    2340
tttttaaaaa ttggaaagga gaaacgaaga ggagatttttt acatgtgagg gatttaattg    2400
taatgcaaat ggtagaaata tataaatgtg aagatatatt cttgaactta aaaacaaact    2460
actaaaataa aaatgaataa aatatttact ctgtcaatat tctgtactat attggtcaat    2520
gaatatttat attattcatg actttaaaaa tagtcaaacc gagacataag gtaaaagtca    2580
aaatacgttt aagctcattc atataaatga atattttttaa attttgttgc atccatcaaa    2640
atatctactt tttaagaatg atatttattt tataatattc atatttgatt cgttgatgga    2700
tagattttat tctgtaagaa attaaataaa aataaaaatt taggcctagt catatccatc    2760
taaaatgggt gagattctgg tacgctgacc gtcttataat tcccaataaa aacttttgga    2820
aaaaaagggt acagaaaata gtgcaccaat agaatcactt ctcacctctt tatagctagt    2880
acggattatt cccttcatgt gtgccacagt catgaacaat ccatattata atttcggaca    2940
taattaattg ttcatatatc tattaacata ataaatttac catttattct ttttacttat    3000
aaagtagata cattaaaaaa tttaagattt ccagaaagtt ctacattttt caaaataatc    3060
aattgagggt ataaaaagt tgtccttcct taatttctca agatgaataa gtaattaaga    3120
acaattaaaa aaagcgaaca aatgaatatt tatcaatcct catttcacca agtcattaaa    3180 ttatttatg acctaaatgt ttactcattt tgcttaaata tcaagaaaat tgttgaatta    3240
tctcttatag aaatatcact caacatcaat atctaattag tactcatttc gttttattt    3300 atatgtcgtt tttattaaaa atagatgttt ttttaatatt tatcatttta caaaatcaaa    3360
atttgactta tgattactaa ataattaatt caatttaatt aatcaaaata aattaattta    3420
tctcttattt aaaagttgac tttaagaaaa caccaattaa aaatataata ataaacttag    3480
ctagtttttt aaaagatata aaatctaaat cagtgacata taaatagaaa cagaggggaa    3540
agtagtagtt taactcttat ggtttgttaa ggtgcgtgct aaatgacaac atctttcttg    3600
tcttgtaaag ttaacatctt agtaggtggt gagtaagtga gtgaatgcca ttgaatgaag    3660
agattatttg ttttttgtcac ctttaccact aaagttttgt ctattttttat tctttgaatt    3720 cctcctgtac aagattttat ttttgatatt cctttctttt ggaattcaga gttggtataa    3780
acaggatcta tttggctatc acacatatat ttttaaacaa aaatcaatat ttagacattt    3840
agttcacatt tcatggatta tactcgttag aaaaagtata tttaagcaat taaatattat    3900
ttgttaaaca tagaaaaatg atttgaaata tattcaaact ttgatcacaa ttgtggtaac    3960
aatttcaaat cttgggaagg accttttatt tcccttgcgc tatttatagt gtattttaaa    4020
tgtatatata tgtcaacata aatatcataa atattacatt attatatata gtaacttgtt    4080
cacgtggaca catgtatacc tgtaaaatat actattaaat agtataggag atagtaggtc    4140
ctgctcaaag ttagagattg ttatagcaat ttcgatcaaa gatatatttc gaactatttt    4200
tcctaaaaga tataaccaaa tacaatttta tctttaattt caaatttgc aaataaagtg    4260 aaaaaaatat ttataccaag taggatgaat taaaaattaa gggttttttt tccttgtcta    4320
tttcttcttg ttatatatat gactaatcat catttttta ttaatgaatc gtcggcaggt    4380
```

```
tggtcactga tattccagct accacaggtt caagttttgg tgagaatcct cttttttgtta    4440 attgtttgtt tgttgtcttc ccatgtttac attttttta aaaaaaaaaa ctaattttaa    4500
aggtagaata aaaaaaaaat cattatcgca tttaaaaata tatgtttata ataacataga    4560
cgaataatat gaaactaacg gagtaatgac aaaggaattt atactgagcg ggcaatgttg    4620
cgttaaatca tgttggtcct aaacttttaa aacctaggaa agggaatgaa atctattctc    4680
aattaacgtg attaaatatt ctaaacaatt gatatccttt aattatgtcc cacactactc    4740
caaaagttct taagcactac actctaaaat ttgtatacat aacattaaaa gatcattacc    4800
tatttggcta aattttttaca ataagtttat tttaaaaagt gttcctttt ttttcctctc    4860 aaaaacacac ttgtgtttct cttgattttt ctctcaaaag tttagttaaa tacttagttt    4920
ttttcaaata atttttttat gaaaaaagaa aaaaaaacat ttttggctaa ccaaacaggt    4980
ttaggagatt tgcgctctgc cataagtatt tccccattca ctttcttcc attttattt    5040 atgattttt ttaacatatt aagaagata tttgtttcat gctcttcatt aatttcttat    5100
cctccaaatt aacatagata ttgtggtaaa acaccataat agttattgta tatttgtata    5160
ccttttcaaa tgtatatact ctctctaatc ctttgttcc ttggtttaag atcacaagat    5220
agataaaaaa acatttattg gtgaataaat ttgacataac tttaatttaa ttatgacacg    5280
aaattcaaaa gttttatttc ttaacttaaa aatttggtgt caagtcagaa gtagatgtga    5340
taattttgtt tttgaaattg gagggagtat cttgttgaaa atattggata tgtacataag    5400
aagtagtcat ttgaaatgca tggaaacttg ataaaaacat aagtagctag ctagtgcatg    5460
aaagtttggt tgtttatgtt cttttaatat gtagggcaag aaatagtgag ctatgaaagt    5520
ccaagaccat caatgggaat acatcgattt gtatttgtat tattcagaca attaggtcga    5580
caaacagtgt atgctccagg atggcgtcag aatttcaaca caagagattt tgcagaactt    5640
tataatcttg gtttacctgt tgctgctgtc tattttaatt gtcaaagaga gagtggcagt    5700
ggtggacgta aagatctgc tgattgatca actccatcta ctacaaaaaa aaaaaaaaaa    5760
aacaatgcat ccctccccct ttttatattt ttagctaata ataaccacca atatctacta    5820
tcactactac ttttcttaca actttagtag tatctatata tatctttttt aatctactct    5880
tttacttctt tactatattg tcttccacac tactatacac tactattgct attatctttc    5940
gtctcaattt atttgaatta gtgacttgat accaagtttc aagaaagaaa taagactga    6000 cttttgaatt ttgtgattta caataagttg tacatatttg tatgactatt ttaaaagttt    6060
aaattattat taaatataat taatttaaaa ggaagtaaat tatataacat gttaattaat    6120
ttttttttaa tttagctttt aaaaagaaag aaaattaaca caattaaaag tattgaatga    6180
aagaagtttg tacctagttt ctgttattcc tctataaaac agtatatttt cttgttactt    6240
ttataaattt ctaagatatg aacttccttg acttttaagt agtattattt agcataaaac    6300
aagttccaat aaggaatctt gagtggaagt acttgtaggg cagtaaaagg gccgcctctt    6360
tgtcaccaaa ccagttgagt ttgctttgga aatacaacag tcgtcatcca acttccttt    6420 ccacaaagcc ttaacagtgg atattaatgt acaaacttac cttcgttcaa atgacgtaca    6480
taattacatt tacattccat catgaaaaat ttgcttcgtc tatctttaat tgtcatgatt    6540
tctattatta taaaattttt aattaacatt ttaatatgta tatattcatc atattgataa    6600
gtaaaaaatt acaagttata gtacttttca tagagttttt gtatatctgt ttttttttaa    6660
aaatatcaaa ttaataataa ctaattcaac tttaaaaatt agtttaatta atttcgaaaa    6720
acgcaaataa caaataaaaa tggaaaagta gataatataa aattaaaata ataaaatctg    6780
```

```
attaaaacta tagtctaatt tatataaagg aaccctaaga atcttctaac ttatccatta    6840
caaaaggatg taatttatgg agttaacaga cgtgtatata gatagacttg aaagtaaaag    6900
aaaactttaa ctctaggaac ttctctataa atacggttgc taggagctcc taataaaatg    6960
tgtctccatc catcaagcaa actacctaca agatatgcat aactttcgcg attcgattcc    7020
tcgagtcatg ataacttcta ttataattca tcaaaggata aattaacccg tatatctaga    7080
acaacaaata attagtacaa gaactaaaca gaaaataata ctaacagaag aagaagacaa    7140
aaacaagatc aaaccaaaac tatatatata tataaaatag aaatcctcca aaaacctgaa    7200
agtcacgagt aaaaaactat ctagtaaaaa taaatacaag tgataaaagt ggaccataac    7260
aagtcatctc aagggcaaaa gactagagtc gacctgcagg ctgcagc                  7307

<210> SEQ ID NO 7
<211> LENGTH: 534
<212> TYPE: DNA
<213> ORGANISM: Lycopersicon esculentum

<400> SEQUENCE: 7
atgcctagag aacgtgatcc tcttgttgtt ggtcgtgtgg tagggatgt attggaccct      60 ttcacaagaa ctattggcct aagagttata tatagagata gagaagttaa taatggatgc    120
gagcttaggc cttcccaagt tattaaccag ccaaggggtg aagttggagg agatgaccta    180
cgtacctttt tcactttggt tatggtggac cctgatgctc caagtccgag tgatccaaat    240
ctgagagaat accttcactg gttggtcacc gatattccag ctaccacagg ttcaagtttt    300
gggcaagaaa tagtgagcta tgaaagtcca agaccatcaa tgggaataca tcgatttgta    360
tttgtattat tcagacaatt aggtcggcaa acagtgtatg ctccaggatg gcgtcagaat    420
ttcaacacaa gagattttgc agaactttat aatcttggtt tacctgttgc tgctgtctat    480
tttaattgtc aaagagagag tggcagtggt ggacgtagaa gatctgctga ttga           534

<210> SEQ ID NO 8
<211> LENGTH: 534
<212> TYPE: DNA
<213> ORGANISM: Lycopersicon pennellii

<400> SEQUENCE: 8
atgcctagag aacgcgatcc tcttgttgtt ggtcgtgtgg tagggatgt attggaccct      60 ttcacaagaa ctattggcct aagagttata tatagagata gagaagttaa taatggatgt    120
gagcttaggc cttcccaagt tattaaccag ccaaggggtg aagttggagg agatgaccta    180
cgtacctttt tcactttggt tatggtggac cctgatgctc caagtccgag tgatccaaat    240
ctgagagaat accttcactg gttggtcact gatattccag ctaccacagg ttcaagtttt    300
gggcaagaaa tagtgagcta tgaaagtcca agaccatcaa tgggaataca tcgatttgta    360
tttgtattat tcagacaatt aggtcgacaa acagtgtatg ctccaggatg gcgtcagaat    420
ttcaacacaa gagattttgc agaactttat aatcttggtt tacctgttgc tgctgtctat    480
tttaattgtc aaagagagag tggcagtggt ggacgtagaa gatctgctga ttga           534

<210> SEQ ID NO 9
<211> LENGTH: 36
<212> TYPE: DNA
<213> ORGANISM: solanum esculenium

<400> SEQUENCE: 9
```
tcttgtgktg tgttttagct cacaaataca caaaag        36

<210> SEQ ID NO 10
<211> LENGTH: 36
<212> TYPE: DNA
<213> ORGANISM: solanum pimpinellifolium

<400> SEQUENCE: 10
tcttgtgttg ggttttagct cacaaataca caaaag        36

<210> SEQ ID NO 11
<211> LENGTH: 36
<212> TYPE: DNA
<213> ORGANISM: solanum pimpinellifolium

<400> SEQUENCE: 11
ycttgkgktg tgttttagct cacaaataca caaaag        36

<210> SEQ ID NO 12
<211> LENGTH: 36
<212> TYPE: DNA
<213> ORGANISM: solanum pimpinellifolium

<400> SEQUENCE: 12
tcttgtgttg tgttttagct cacaaataca caaaag        36

<210> SEQ ID NO 13
<211> LENGTH: 36
<212> TYPE: DNA
<213> ORGANISM: solanum cheesmanii

<400> SEQUENCE: 13
ycttgkgttg ggttttagct cacaaataca caaaag        36

<210> SEQ ID NO 14
<211> LENGTH: 36
<212> TYPE: DNA
<213> ORGANISM: solanum cheesmanii

<400> SEQUENCE: 14
tcttgtgttg kgttttagct cacaaataca caaaag        36

<210> SEQ ID NO 15
<211> LENGTH: 36
<212> TYPE: DNA
<213> ORGANISM: solanum cheesmanii

<400> SEQUENCE: 15
tcttgtgttg tgttttagct cacaaataca caaaag        36

<210> SEQ ID NO 16
<211> LENGTH: 36
<212> TYPE: DNA
<213> ORGANISM: solanum cheesmanii

<400> SEQUENCE: 16
tcttgtgttg tgttttagct cacaaataca caaaag        36

<210> SEQ ID NO 17
<211> LENGTH: 36
<212> TYPE: DNA
<213> ORGANISM: solanum cheesmanii

<400> SEQUENCE: 17

-continued

```
tcttgtgttg tgttttagct cacaaataca caaaag                                    36

<210> SEQ ID NO 18
<211> LENGTH: 36
<212> TYPE: DNA
<213> ORGANISM: solanum cheesmanii

<400> SEQUENCE: 18
tcttgtgttg tgttttagct cacaaataca caaaag                                    36

<210> SEQ ID NO 19
<211> LENGTH: 36
<212> TYPE: DNA
<213> ORGANISM: solanum cheesmanii

<400> SEQUENCE: 19
tcttgtgttg tgttttagct cacaaataca caaaag                                    36

<210> SEQ ID NO 20
<211> LENGTH: 36
<212> TYPE: DNA
<213> ORGANISM: solanum cheesmanii

<400> SEQUENCE: 20
tcttgtgttg tgttttagct cacaaataca caaaag                                    36

<210> SEQ ID NO 21
<211> LENGTH: 36
<212> TYPE: DNA
<213> ORGANISM: solanum cheesmanii

<400> SEQUENCE: 21
tcttgtgttg tgttttagct cacaaataca caaaag                                    36

<210> SEQ ID NO 22
<211> LENGTH: 36
<212> TYPE: DNA
<213> ORGANISM: solanum cheesmanii

<400> SEQUENCE: 22
tcttgtgttg tgttttagct cacaaataca caaaag                                    36

<210> SEQ ID NO 23
<211> LENGTH: 36
<212> TYPE: DNA
<213> ORGANISM: solanum cheesmanii

<400> SEQUENCE: 23
tcttgtgttg tgttttagct cacaaataca caaaag                                    36

<210> SEQ ID NO 24
<211> LENGTH: 43
<212> TYPE: DNA
<213> ORGANISM: solanum habrochaites

<400> SEQUENCE: 24
brchatstct tgtgttgtgt tttagtacac aaatacacaa aag                            43

<210> SEQ ID NO 25
<211> LENGTH: 36
<212> TYPE: DNA
<213> ORGANISM: solanum habrochaites
```

```
<400> SEQUENCE: 25
tcttgtgttg tgttttagta cacaaataca caaaag                    36

<210> SEQ ID NO 26
<211> LENGTH: 36
<212> TYPE: DNA
<213> ORGANISM: solanum habrochaites

<400> SEQUENCE: 26
tcttgtgttg tgttttagta cacaaataca caaaag                    36

<210> SEQ ID NO 27
<211> LENGTH: 36
<212> TYPE: DNA
<213> ORGANISM: solanum habrochaites

<400> SEQUENCE: 27
tcttgtgttg tgttttagta cacaaataca caaaag                    36

<210> SEQ ID NO 28
<211> LENGTH: 36
<212> TYPE: DNA
<213> ORGANISM: solanum habrochaites

<400> SEQUENCE: 28
tcttgtgttg tgttttagta cacaaataca caaaag                    36

<210> SEQ ID NO 29
<211> LENGTH: 36
<212> TYPE: DNA
<213> ORGANISM: solanum habrochaites

<400> SEQUENCE: 29
tcttgtgttg tgttttagta cacaaataca caaaag                    36

<210> SEQ ID NO 30
<211> LENGTH: 36
<212> TYPE: DNA
<213> ORGANISM: solanum habrochaites

<400> SEQUENCE: 30
tcttgtgttg tgttttagta cacaaataca caaaag                    36

<210> SEQ ID NO 31
<211> LENGTH: 36
<212> TYPE: DNA
<213> ORGANISM: solanum pennellii

<400> SEQUENCE: 31
tcttgtgttg tgttttagca cacaaataca caaaag                    36

<210> SEQ ID NO 32
<211> LENGTH: 36
<212> TYPE: DNA
<213> ORGANISM: solanum parviflorum

<400> SEQUENCE: 32
tcttgtgttg tgttttagca cacaaataca caaaag                    36

<210> SEQ ID NO 33
<211> LENGTH: 36
<212> TYPE: DNA
<213> ORGANISM: solanum peruvianum
```

```
<400> SEQUENCE: 33
tcttgtgttg tgttttagca cacaaataca caaaag                                    36

<210> SEQ ID NO 34
<211> LENGTH: 36
<212> TYPE: DNA
<213> ORGANISM: solanum peruvianum

<400> SEQUENCE: 34
tcttgtgttg tgttttagca cacaaataca caaaag                                    36

<210> SEQ ID NO 35
<211> LENGTH: 36
<212> TYPE: DNA
<213> ORGANISM: solanum peruvianum

<400> SEQUENCE: 35
tcttgtgttg tgttttagca cacaaataca gaaaag                                    36

<210> SEQ ID NO 36
<211> LENGTH: 36
<212> TYPE: DNA
<213> ORGANISM: solanum peruvianum

<400> SEQUENCE: 36
tcttgtgttg tgttttagca cacaaataca caaaag                                    36

<210> SEQ ID NO 37
<211> LENGTH: 36
<212> TYPE: DNA
<213> ORGANISM: solanum peruvianum

<400> SEQUENCE: 37
tcttgtgttg tgttttagca cacaaataca caaaag                                    36

<210> SEQ ID NO 38
<211> LENGTH: 36
<212> TYPE: DNA
<213> ORGANISM: solanum peruvianum

<400> SEQUENCE: 38
tcttgtgttg tgttttagca cacaaataca caaaag                                    36

<210> SEQ ID NO 39
<211> LENGTH: 36
<212> TYPE: DNA
<213> ORGANISM: solanum parviflorum

<400> SEQUENCE: 39
tcttgtgttg tgttttagca cacaaataca caaaag                                    36

<210> SEQ ID NO 40
<211> LENGTH: 36
<212> TYPE: DNA
<213> ORGANISM: solanum parviflorum

<400> SEQUENCE: 40
tcttgtgttg tgttttagca cacaaataca caaaag                                    36

<210> SEQ ID NO 41
<211> LENGTH: 36
<212> TYPE: DNA
```

<213> ORGANISM: solanum parviflorum

<400> SEQUENCE: 41
tcttgtgttg tgttttagca cacaaataca caaaag     36

<210> SEQ ID NO 42
<211> LENGTH: 36
<212> TYPE: DNA
<213> ORGANISM: solanum parviflorum

<400> SEQUENCE: 42
tcttgtgttg tgttttagca cacaaataca caaaag     36

<210> SEQ ID NO 43
<211> LENGTH: 36
<212> TYPE: DNA
<213> ORGANISM: solanum parviflorum

<400> SEQUENCE: 43
tcttgtgttg tgttttagca cacaaataca caaaag     36

<210> SEQ ID NO 44
<211> LENGTH: 36
<212> TYPE: DNA
<213> ORGANISM: solanum parviflorum

<400> SEQUENCE: 44
tcttgtgttg tgttttagca cataaataca caaaag     36

<210> SEQ ID NO 45
<211> LENGTH: 36
<212> TYPE: DNA
<213> ORGANISM: solanum parviflorum

<400> SEQUENCE: 45
tcttgtgttg tgttttagca cacaaataca caaaag     36

<210> SEQ ID NO 46
<211> LENGTH: 36
<212> TYPE: DNA
<213> ORGANISM: solanum parviflorum

<400> SEQUENCE: 46
tcttgtgttg tgttttagca cacaaataca caaaag     36

<210> SEQ ID NO 47
<211> LENGTH: 36
<212> TYPE: DNA
<213> ORGANISM: solanum parviflorum

<400> SEQUENCE: 47
tcttgtgttg tgttttagca cataaataca caaaag     36

<210> SEQ ID NO 48
<211> LENGTH: 36
<212> TYPE: DNA
<213> ORGANISM: solanum parviflorum

<400> SEQUENCE: 48
tcttgtgttg tgttttagca cacaaataca caaaag     36

<210> SEQ ID NO 49
<211> LENGTH: 36

```
<212> TYPE: DNA
<213> ORGANISM: solanum chmielewskii

<400> SEQUENCE: 49
tcttgtgttg tgttttagca cacaaataca caaaag                                    36

<210> SEQ ID NO 50
<211> LENGTH: 36
<212> TYPE: DNA
<213> ORGANISM: solanum chmielewskii

<400> SEQUENCE: 50
tcttgtgttg tgttttagca cacaaataca caaaag                                    36

<210> SEQ ID NO 51
<211> LENGTH: 36
<212> TYPE: DNA
<213> ORGANISM: solanum chmielewskii

<400> SEQUENCE: 51
tcttgtgttg tgttttagca cacaaataca caaaag                                    36

<210> SEQ ID NO 52
<211> LENGTH: 36
<212> TYPE: DNA
<213> ORGANISM: solanum chmielewskii

<400> SEQUENCE: 52
tcttgtgttg tgttttagca cacaaataca caaaag                                    36

<210> SEQ ID NO 53
<211> LENGTH: 36
<212> TYPE: DNA
<213> ORGANISM: solanum chmielewskii

<400> SEQUENCE: 53
tcttgtgttg tgttttagca cacaaataca caaaag                                    36

<210> SEQ ID NO 54
<211> LENGTH: 36
<212> TYPE: DNA
<213> ORGANISM: solanum chmielewskii

<400> SEQUENCE: 54
tcttgtgttg tgttttagca cacaaataca caaaag                                    36

<210> SEQ ID NO 55
<211> LENGTH: 36
<212> TYPE: DNA
<213> ORGANISM: solanum chmielewskii

<400> SEQUENCE: 55
tcttgtgttg tgttttagca cacaaataca caaaag                                    36

<210> SEQ ID NO 56
<211> LENGTH: 36
<212> TYPE: DNA
<213> ORGANISM: solanum chmielewskii

<400> SEQUENCE: 56
tcttgtgttg tgttttagca cacaaataca caaaag                                    36

<210> SEQ ID NO 57
```

```
<211> LENGTH: 36
<212> TYPE: DNA
<213> ORGANISM: solanum chmielewskii

<400> SEQUENCE: 57
tcttgtgttg tgttttagca cacaaataca caaaag                              36

<210> SEQ ID NO 58
<211> LENGTH: 36
<212> TYPE: DNA
<213> ORGANISM: solanum chmielewskii

<400> SEQUENCE: 58
tcttgtgttg tgttttagca cacaaataca caaaag                              36

<210> SEQ ID NO 59
<211> LENGTH: 36
<212> TYPE: DNA
<213> ORGANISM: solanum chmielewskii

<400> SEQUENCE: 59
tcttgtgttg tgttttagca cacaaataca caaaag                              36

<210> SEQ ID NO 60
<211> LENGTH: 36
<212> TYPE: DNA
<213> ORGANISM: solanum chilense

<400> SEQUENCE: 60
tcttgtgttg tgttttagca cacaaataca caaaag                              36

<210> SEQ ID NO 61
<211> LENGTH: 36
<212> TYPE: DNA
<213> ORGANISM: solanum chilense

<400> SEQUENCE: 61
tcttgtgttg tgttttagca cacaaataca caaaag                              36

<210> SEQ ID NO 62
<211> LENGTH: 176
<212> TYPE: PRT
<213> ORGANISM: Lycopersicon esculentum

<400> SEQUENCE: 62

Met Pro Arg Glu Arg Asp Pro Leu Val Val Gly Arg Val Gly Asp
1               5                   10                  15

Val Leu Asp Pro Phe Thr Arg Thr Ile Gly Leu Arg Val Ile Tyr Arg
            20                  25                  30

Asp Arg Glu Val Asn Asn Gly Cys Glu Leu Arg Pro Ser Gln Val Ile
        35                  40                  45

Asn Gln Pro Arg Val Glu Val Gly Gly Asp Asp Leu Arg Thr Phe Phe
    50                  55                  60

Thr Leu Val Met Val Pro Asp Ala Pro Ser Pro Ser Asp Pro Asn Leu
65                  70                  75                  80

Arg Glu Tyr Leu His Trp Leu Val Thr Asp Ile Pro Ala Thr Thr Gly
                85                  90                  95

Ser Ser Phe Gly Gln Glu Ile Val Ser Tyr Glu Ser Pro Arg Pro Ser
            100                 105                 110

Met Gly Ile His Arg Phe Val Phe Val Leu Phe Arg Gln Leu Gly Arg
        115                 120                 125
```

-continued

```
Gln Thr Val Tyr Ala Pro Gly Trp Arg Gln Asn Phe Asn Thr Arg Asp
        130                 135                 140

Phe Ala Glu Leu Tyr Asn Leu Gly Leu Pro Val Ala Ala Val Tyr Phe
145                 150                 155                 160

Asn Cys Gln Arg Glu Ser Gly Ser Gly Gly Arg Arg Arg Ser Ala Asp
                165                 170                 175

<210> SEQ ID NO 63
<211> LENGTH: 176
<212> TYPE: PRT
<213> ORGANISM: Lycopersicon pennellii

<400> SEQUENCE: 63

Met Pro Arg Glu Arg Asp Pro Leu Val Val Gly Arg Val Val Gly Asp
1               5                   10                  15

Val Leu Asp Pro Phe Thr Arg Thr Ile Gly Leu Arg Val Ile Tyr Arg
            20                  25                  30

Asp Arg Glu Val Asn Asn Gly Cys Glu Leu Arg Pro Ser Gln Val Ile
        35                  40                  45

Asn Gln Pro Arg Val Glu Val Gly Gly Asp Asp Leu Arg Thr Phe Phe
    50                  55                  60

Thr Leu Val Met Val Pro Asp Ala Pro Ser Pro Ser Asp Pro Asn Leu
65                  70                  75                  80

Arg Glu Tyr Leu His Trp Leu Val Thr Asp Ile Pro Ala Thr Thr Gly
                85                  90                  95

Ser Ser Phe Gly Gln Glu Ile Val Ser Tyr Glu Ser Pro Arg Pro Ser
            100                 105                 110

Met Gly Ile His Arg Phe Val Phe Val Leu Phe Arg Gln Leu Gly Arg
        115                 120                 125

Gln Thr Val Tyr Ala Pro Gly Trp Arg Gln Asn Phe Asn Thr Arg Asp
    130                 135                 140

Phe Ala Glu Leu Tyr Asn Leu Gly Leu Pro Val Ala Ala Val Tyr Phe
145                 150                 155                 160

Asn Cys Gln Arg Glu Ser Gly Ser Gly Gly Arg Arg Arg Ser Ala Asp
                165                 170                 175
```

PROMOTOR SEQUENCE AND GENE CONSTRUCT FOR INCREASING CROP YIELD IN TOMATO

The Sequence Listing associated with this application is filed in electronic format via EFS-Web and is hereby incorporated by reference into the specification in its entirety. The name of the text file containing the Sequence Listing is 123318_ST25.txt. The size of the text file is 23,640 bytes, and the text file was created on Jan. 24, 2014.

TECHNICAL FIELD

The present invention relates to a promotor sequence which, when operably linked to a downstream plant gene in a plant, is capable of increasing crop yield in said plant, in particular in tomato. The invention further relates to plants of the Solanaceae family, in particular to tomato plants (*Solanum lycopersicum*), comprising said promotor sequence operably linked to said downstream plant gene, to methods for obtaining said plants and to plants obtainable by such methods.

BACKGROUND OF THE INVENTION

Tomato (*Solanum lycopersicum*, also called *Lycopersicon esculentum*) is a plant of the Solanaceae or nightshade family. It is a short-lived perennial plant, grown as an annual plant, and a close relative of the potato. The fruit (i.e. the tomato) is an edible, brightly coloured (usually red, from the pigment lycopene) berry, 1-2 cm diameter in wild plants, commonly much larger in cultivated forms. The plant is now grown worldwide for its edible fruits, which are major fresh market vegetables worldwide.

The growth habit of tomato plants is commonly classified as determinate or indeterminate. This classification depends on the capacity of the shoot system for continued sympodial growth. Indeterminate cultivars (where the apical meristem grows indefinitely and flowers arise from the axillary meristem) produce branched systems that grow indefinitely, whereas determinate cultivars (where apical meristem is converted into terminal flower) produce branching systems with progressively fewer nodes until the shoot terminates with two inflorescences and develops the form of a bush. This change in plant architecture is due to a mutation in the SELF-PRUNING (SP) gene (Pnueli et al., Development 125: 1979-1989, 1998) and has been an important development for this crop, because determinate types can be harvested mechanically and are therefore mainly used for the processing industry, whereas indeterminate types are generally grown in greenhouses and are used for the fresh market.

Fridman et al. (Mol. Genet. Genomics 266: 821-826, 2002) previously have shown that introgression of a *S. Pennellii* allele of a QTL named PW9-2-5 in a sp/sp *S. Esculentum* background results in a semi-determinate growth with 2 leaves between the trusses (designated as spi=2). They suggested that the SP9D gene from *S. Penellii*, SP9Dpen, is the candidate gene for the change of plant architecture and also the so-called Solid Solid Content (SSC) or the refractive index (which is indirectly related to the taste). The SP9D gene belongs to the CETS gene family (CENTRORADIALIS, Terminal Flower) and it is believed that this gene family plays a key role in determining plant architecture (Carmel-Goren, Plant Mol. Biol. 52; 1215-1222, 2003).

*S. lycopersicum* has six CETS gene family members, named SP, distributed over five different chromosomes: SP2I, SP3D, SP5G, SP6A, and SP9D, wherein the names are given according to the bin position (Pan et al., Genetics 155: 309-322, 2000). The sixth member, SP, is located on chromosome 6, bin E, and is known to be the gene that alters the tomato in a determinate (sp/sp)/indeterminate (SP/−) phenotype. Phylogenetic relationships grouped SP3D, SP5G, and SP6A with the *Arabidopsis* FT gene. SP9D and SP are grouped with *Arabidopsis* TFL-1, and SP2I is in the same branch with the Mother of Flowering Time (MFT) of *Arabidopsis* (Carmel-Goren et al., supra). Despite the phylogenetic relationships between the genes, the expression profiles differ. Thus, SP5G expression has been found predominantly in cotelydons, whereas SP3D is expressed mainly in floral organs with low expression in vegetative organ leaves. For SP6A no expression has been found sofar. SP9D is mainly expressed in the shoot apex and has a high expression in roots, whereas SP2I is expressed in all organs tested. In spite of these expression profiles little is known about their function with SP as an exception.

During the last decades, indeterminate tomato breeding was mainly focussed on yield, disease resistance, and fruit quality aspects such as uniform ripening and taste. Yield improvements have been achieved due to new production methods, improved pest management and varieties that are better suited for new production methods, but the gains in yield become smaller. New varieties with 5 or 15 fruits more per plant gave a yield increase of 2-4%.

Development of varieties with higher yield was hampered by the lack of knowledge regarding the aspects that determine tomato yield. Xiao (2004; ISHS Acta Horticulturae 654 (International workshop on models for plant growth and control of product quality in horticultural production) and Heuvelink (2005; ISHS Acta Horticulturae 691 (International Conference on sustainable greenhouse systems—greensys2004; 43-50) simulated that a tomato variety with two leaves between trusses instead of the conventional three leaves would shift assimilation towards the fruits, resulting in higher yields when the Leaf Area Index (LAI) is maintained. They validated the simulated data by removing every second leaf and keeping the LAI above 3. As simulated, the yield increased by roughly 10%.

Cultivated varieties with two leaves between the trusses are not known, however, there are wild tomato relatives with two leaves between the trusses, i.e. having a sympodial index=2 (spi=2), such as *Solanum neorickii, Solanum chmielewskii, Solanum chilense, Solanum peruvianum*, and *Solanum pennellii*. The property of a sympodial index of 2 is recessive to the sympodial index of 3 in cultivated tomatoes of F1 hybrids of the inter-species cross with *S. penellii* (Pnueli et al., 1998, supra). The genetic basis of spi=2, however, sofar is not known.

As the world population continues to grow, the demand for fresh vegetables, such as tomatoes, is ever increasing worldwide. Thus, a continuing need exists for means and methods for improving yield of vegetable plants, such as tomato.

SUMMARY OF THE INVENTION

The object of the present invention is to provide novel means and methods for increasing crop yield in plants of the Solanaceae family.

The object of the present invention in particular is to provide novel means and methods for increasing crop yield in tomato, *S. lycopersicum*.

This object is achieved by providing a SP3D promotor sequence, which is capable of directing transcription of a downstream SP3D gene that is operably linked to said promotor sequence, wherein the promotor sequence is derived from a species of the Solanaceae family, having a sympodial index of 2, for reducing sympodial index in plants having a sympodial index of 3 or more.

In a preferred embodiment, the promotor sequence comprises a CA motif at a position 62-61 nucleotides upstream (i.e. at positions −62 and −61 nt) of the start codon of said SP3D gene.

In another preferred embodiment of the invention, said promotor sequence comprises a nucleotide sequence having at least 75% identity with nucleotides 1251 to 1874 of SEQ ID NO: 6 (FIG. 2).

According to a further preferred embodiment of the invention, the promotor sequence comprises a nucleotide sequence having at least 85%, more preferably at least 90%, more preferably at least 95%, and most preferably at least 99% identity with nucleotides 1251 to 1874 of SEQ ID NO: 6.

BRIEF DESCRIPTION OF THE DRAWINGS

The invention is further illustrated by the following Examples and Figures.

FIG. 1 shows the primer sequences used for screening a S. pennellii BAC library and selection of plants, including dSP3D f1 (SEQ ID NO: 1), dSP3D r1 (SEQ ID NO: 2), sp3d 10fa (SEQ ID NO: 3), SP3D f2 (SEQ ID NO: 4), and SP3D R (SEQ ID NO: 5).

FIG. 2 shows the nucleotide sequence of SEQ ID NO: 6, i.e. the genomic nucleotide sequence of the SP3Dpen gene including the promoter sequence (nucleotides 1251-1874). The CA motif has been indicated in bold and underlined; the grey boxes and double underlined region indicates the SP3D codon, lower case indicates a SNP in the CDS compared to S. lycopersicum.

FIG. 4 shows the alignment of the SP3Dpen promoter region of nucleotides 544-580 (SEQ ID NO: 9) with other wild relatives of the Solanaceae family, including S. pimpinellifolium (SEQ ID NOs. 10-12), S. cheesmanii (SEQ ID NOs. 13-23) S. habrochaites (SEQ ID NOs. 24-30), S. pennellii (SEQ ID NO: 31), S. parviflorum (SEQ ID NOs 32 and 40-48), S. peruvianum (SEQ ID NOs. 33-39), S. chmielewskii (SEQ ID NOs. 49-59), and S. chilense (SEQ ID NOs. 60 and 61), indicating that the CT or TA motifs indicated with an arrow are linked with spi=3 and a CA motif is associated with spi=2.

FIG. 7 is a table wherein the phenotypes for homozygous and heterozygous F1 hybrids are compared. The results given are the average results of 4 plants. 15751 is a S. lycopersicum plant of the invention, which comprises the promoter of the present invention in operable linkage with the SP3D gene in homozygous form, 15753 is a S. lycopersicum plant of the invention, which comprises the promoter/SP3D gene in heterozygous form. It is clear that both homozygous and heterozygous plants have a reduced sympodial index as compared to the plant 15769, which is a normal S. lycopersicum plant not comprising the promotor/SP3D gene genetic constitution of the invention. SPI is sympodial index. # fruits is the total number of harvestable fruits, trusses is the total number of trusses formed during the examination period (i.e. a total of 4 months) and "# leaves 1 truss" is the total number of leaves until the first truss.

DETAILED DESCRIPTION OF THE INVENTION

Figure 3:
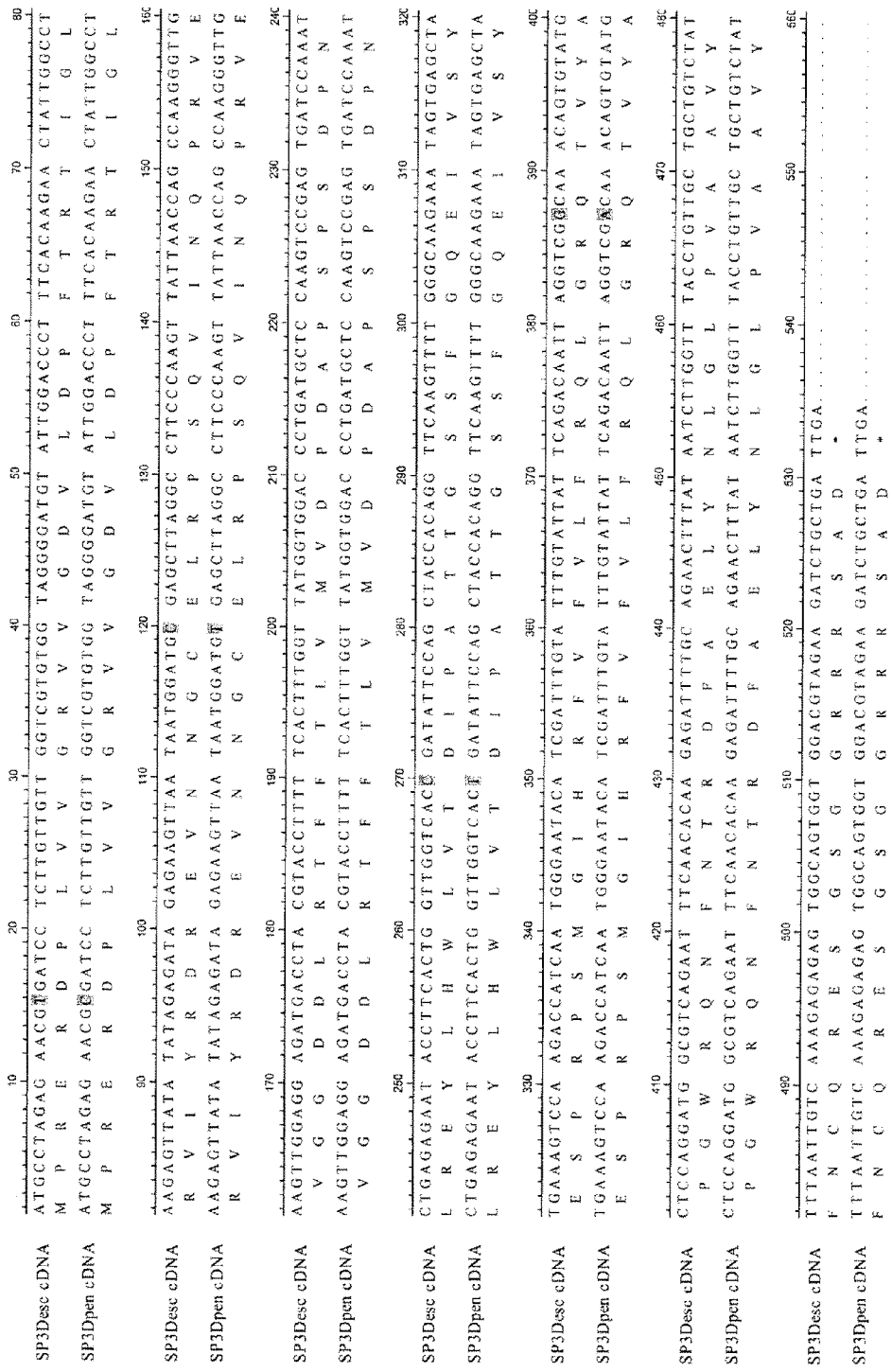
FIG. 3 shows the alignment of SP3Desc cDNA (SEQ ID NO: 7) and its amino acid translation (SEQ ID NO: 62) (i.e. derived from S. lycopersicum (also known as L. esculentum)) with SP3Dpen cDNA (SEQ ID NO: 8) and its amino acid translation (SEQ ID NO: 63), indicating that the 4 nucleotide changes (grey boxes) in the coding regions are synonymous.

In the research that has led to the present invention, a novel gene of the CETS gene family that gives rise to spi=2 was identified. Thus, introgression line 49015-2 containing a S. pennellii La716 insertion from chromosome 3 was demonstrated to give a sympodial index of 2. Based on map location and phenotype it was concluded that the property of spi=2 from line 49015-2 is caused by the SP3D gene from S. pennellii, which has been designated "SP3Dpen".

According to the invention, it was subsequently found that the property of spi=2 was not caused by the gene itself but was due to regulation of the gene by said promotor. In particular, it was demonstrated that the sympodial index of 2 was linked to a CA motif in the promoter sequence 62-61 nt upstream of the start of the SP3D gene, i.e. the nucleotide at position −62 is C and the nucleotide on position −61 is A.

As described above, in the sympodial shoots of tomato (S. lycopersicum) the vegetative and reproductive phases alternate regularly. The primary shoot normally occurs after the production of 8-10 leaves and growth then continues from the uppermost lateral (axillary) bud just below the inflorescences. This shoot then generally generates three more leaves before terminating in turn with another florescence and so on. Thus, the shoot is predominantly composed of a number of reiterated sympodial units each consisting of three vegetative nodes and a terminal inflorescence, which is referred to as having a sympodial index of 3 (spi=3).

According to the present invention it has now been found that by introducing one of the above-described promotor sequences in operable linkage with a SP3D gene in a plant of the Solanaceae family having a sympodial index of 3 or more, a plant results having a reduced sympodial index as compared to plants not having said promotor.

In a preferred embodiment the sympodial index is reduced to a sympodial index of 2. Thus, preferably a plant results having a sympodial index of 2, i.e. plant of which the shoot is predominantly composed of sympodial units consisting of two vegetative nodes and a terminal inflorescence. According to the present invention, a "sympodial index of 2" relates to an average sympodial index between and including 1.6 and 2.5, preferably between 1.6 and 2.5, more preferably between 1.7 and 2.4, even more preferably between 1.8 and 2.3, most preferably between 1.9 and 2.2.

According to the invention, it has thus been found that the promotor sequence, when operably linked to a SP3D gene, leads to an increased crop yield in plants. Thus, for example, a plant having a sympodial index which is reduced from 3 to 2, will predominantly have two leaves between the trusses instead of three, such that the sympodia are roughly ⅓ shorter than the spi=3 counterpart, which will lead to an increased number of trusses per unit of length of the plant.

In addition, the successive trusses will appear earlier in time, such that also an increased number of trusses per time unit is obtained. Furthermore, It has been found that the promotor sequence leads to an increased crop yield without the semi-determinate growth habit of SP9Dpen.

Moreover, the promotor, when operably linked to the SP3D gene, gives rise to several other beneficial traits such as the occurrence of a first truss after 6-8 leaves instead of approximately 10 leaves. Furthermore, more fruits per truss (roughly one fruit more per truss) could be maintained in these plants. These characteristics result in an increased number of fruit clusters per meter or time unit and/or an increased number of fruits per cluster and therefore a higher crop yield.

It is noted that according to the present invention, the term "crop yield" is defined as the amount (for example expressed in kg) of product (for example fruit, e.g. tomatoes) per meter of shoot and branches of the plant, or per time unit (from initial planting till end of crop or termination of growth season, for example expressed in months). An increase in crop yield of plants comprising the promotor sequence of the invention relates to the increase in crop yield as compared to the crop yield of the same plants not comprising the promotor sequence of the invention.

In a particularly preferred embodiment of the invention, the promotor sequence is derived from a species of the Solanaceae family selected from the group consisting of *Solanum pennellii*, *Solanum neorickii*, *Solanum chmielewskii*, *Solanum chilense*, and *Solanum peruvianum*.

In another preferred embodiment of the invention, said promotor sequence comprises a nucleotide sequence having at least 75% identity with nucleotides 1251 to 1874 of SEQ ID NO: 6 (FIG. 2).

According to a further preferred embodiment of the invention, the promotor sequence comprises a nucleotide sequence having at least 85%, more preferably at least 90%, more preferably at least 95%, and most preferably at least 99% identity with nucleotides 1251 to 1874 of SEQ ID NO: 6.

According to the present invention, the wording "a nucleotide sequence having X % identity" relates to a nucleotide sequence having a nucleotide sequence of which X % of the nucleotides is identical to the specific nucleotide sequence (i.e. nucleotides 1251 to 1874) of SEQ ID NO: 6. This may thus encompass nucleotides sequences having the same number of 624 nucleotides, but wherein X % of the nucleotides is different as compared to nucleotides 1251 to 1874 of said SEQ ID NO: 6 and/or fragments of said part of SEQ ID NO: 6, comprising X % of the original nucleotides (a mixed form is also possible). It should be understood that in all cases the CA motif should be present and the promotor should have promotor activity.

In a particularly preferred embodiment, the promotor sequence is derived from *S. Pennellii* and consists of the nucleotide sequence of nucleotides 1251 to 1874 of SEQ ID NO: 6.

It has thus been found according to the present invention that plants of the Solanaceae family, in particular *S. lycopersicum*, comprising the promotor sequence of the present invention, as defined above, in operable linkage with a SP3D gene, yield more kg of fruit, per meter of shoot and branches and/or per time unit, as compared to the same plants not comprising the promotor sequence of the invention.

It was previously reported by Lifschitz et al. (PNAS 103, 6398-6403, 2006) that the SP3D gene is the causal gene for the sft (single-flower truss) tomato mutant. The sft mutant plants are late flowering with a reduced number of flowers per inflorescence (1 or 2 flowers per truss) and have an indeterminate inflorescence. It was shown that the single-flower truss (sft) mutation is due to mutations in the SP3D gene. It was shown that plants highly expressing SFT under the control of the constitutive 35S promoter maintained the sympodial growth pattern but had a sympodial index of 2 instead of 3. Grafting of a sft mutant scion on 35S:SFT rootstock rescued the wild type phenotype (including spi=3), demonstrating that SP3D/SFT mediates its function by a systemic signal. The promotor sequence according to the present invention and its influence on the sympodial index, and consequently on crop yield of plants of the Solanaceae family, in particular of *S. lycopersicum*, have not been disclosed by Lifschitz et al.

The promotor sequence of the present invention may be introduced in operably linkage with any active SP3D gene.

In a preferred embodiment, the SP3D gene comprises a genomic nucleotide sequence having at least 75% identity with nucleotides 1875 to 7307 of SEQ ID NO: 6. Preferably the sequence identity is 85%, more preferably 90%, even more preferably 95%, and most preferably 99%. The invention also relates to these SP3D genes per se.

In a particular preferred embodiment, the SP3D gene is the SP3D gene of *S. pennellii*, SP3Dpen, having a genomic nucleotide sequence consisting of nucleotides 1875 to 7307 of SEQ ID NO: 6.

The present invention also relates to a gene construct, comprising a promotor sequence as described above and a cDNA sequence derived from a SP3D gene as described above. Such gene construct may for example be introduced into plants using known molecular biological techniques, in order to provide genetically, modified plants of the Solanaceae family, preferably *S. lycopersicum*, having a reduced sympodial index.

In a preferred embodiment, the cDNA sequence comprises a nucleotide sequence having at least 75% identity with the cDNA sequence of SP3Dpen as shown in FIG. 3. Preferably the sequence identity is 85%, more preferably, 90%, even more preferably 95% and most preferably 99%.

In a particularly preferred embodiment, the cDNA sequence consists of the nucleotide sequence as shown in FIG. 3.

The invention further relates to a method for providing plants of the Solanaceae family having a reduced sympodial index, comprising of introducing into the genome of a plant of the Solanaceae family having a sympodial index of 3 or more, a promotor sequence as described above in operable linkage with a downstream SP3D gene, or introducing into said plant a gene construct as described above, such that a plant results having a reduced sympodial index as compared to said plant without said promotor sequence.

In a preferred embodiment the sympodial index is reduced to a sympodial index of 2.

The invention further relates to a method for increasing crop yield in a plant of the Solanaceae family having a sympodial index of 3 or more, comprising of introducing into the genome of said plant a promotor sequence as described above, in operable linkage with a downstream SP3D gene, or introducing into said plant a gene construct as described above.

In preferred embodiments of the above-identified methods the plant is preferably selected from the group consisting of *S. habrochaites*, *S. cheesmaniae*, *S. pimpinellifolium* and *S. lycopersicum*, and/or plants derived therefrom. In a particularly preferred embodiment, the plant is *S. lycopersicum*. The term "plants derived therefrom" relates for example to plants derived from crossing two selected species, such as, for example, plants derived from a crossing between *S. habrochaites* and *S. lycopersicum*.

The promotor sequence, and/or the gene construct may be introduced into these plants by introgression through conventional breeding techniques, such as described below, or alternatively, by using suitable molecular biological techniques, which are well known to the skilled person. Introduction of the promotor sequence, or introduction of a suitable gene construct, comprising the promotor sequence and a cDNA sequence of a SP3D gene of the invention, into plant cells can for instance be effected by transfection, microinjection, electroporation, etc. It is also possible to use *Agrobacterium* mediated transformation. The cells may then subsequently be regenerated into whole plants.

According to the invention, it has been shown that by introducing the promotor sequence of the invention in operable linkage with a SP3D gene, or by introducing the gene construct of the invention in species of the Solanaceae family, that normally (i.e. without the promotor sequence) would have a sympodial index of 3 or more, for example a sympodial index of 3, now plants can be obtained having a reduced sympodial index, preferably a sympodial index of 2, which will lead to an increase in crop yield.

In addition, it has been found that, in the case of tomato, *S. lycopersicum*, the first truss occurs after 6-8 leaves instead of approximately 10 leaves. Furthermore, more fruits per truss (roughly one fruit more per truss) could be maintained in these plants. Thus, plants are obtained which will lead to an increased crop yield as compared to the same plants, not comprising the promotor sequence.

The promotor sequence of the invention may be introduced in operable linkage with a SP3D gene that is endogenous to the plant, i.e. with the SP3D gene that normally exists in said plant. In this case, only the promotor sequence is introduced, i.e. the endogenous promotor sequence is replaced by a selected recombinant of the promotor sequence of the invention, which is in operable linkage with the endogenous SP3D gene of said plant. It is, however, also possible to introduce both the promotor and the SP3D gene, or a gene construct according to the present invention as defined above. In case both the promotor and the SP3D gene are introduced in the plant, both are thus exogenous to said plant.

The invention furthermore relates to plants of the Solanaceae family, obtainable by said method, and having a reduced sympodial index, preferably having a sympodial of 2, as well as to seeds and other plant parts derived there from, such as plant cells, organs, and tissues, such as for example rootstocks. Normal practice in tomato breeding involves grafting of a tomato variety on a disease resistant rootstock to control soil-born diseases. Rootstocks generally are more vigorous than non-grafted tomatoes. Grafting may for example be executed on the epicotyls, before the first leaves, on a *S. lycopersicum*×wild relative hybrid.

The plant of the invention preferably is selected from the group consisting of *S. habrochaites, S. cheesmaniae, S. pimpinellifolium* and *S. lycopersicum*, and/or plants derived therefrom. In a particularly preferred embodiment, the plant is *S. lycopersicum*.

The invention furthermore also relates to a plant of the Solanaceae family, in particular plants normally having a sympodial index of 3 or more, comprising in its genome a promotor sequence as described above, in operable linkage with a SP3D gene, and thereby having a reduced sympodial index, preferably having a sympodial index of 2. Again, the SP3D gene may be endogenous or exogenous to the plant. The invention also relates to plant seeds and/or other plant parts as described above, derived from said plant.

The plant preferably is selected from the group of *S. habrochaites, S. cheesmaniae, S. pimpinellifolium* and *S. lycopersicum*, and/or plants derived therefrom, Preferably, the plant is *S. lycopersicum*.

EXAMPLES

Example 1

Cloning and Isolation of SP3Dpen

SP3D *Solanum esculentum* gene (accession number AY186735) has been used for cloning the *Solanum pennelii* la716 gene. A *S. pennellii* BAC library has been screened with primers SP3D-f2/SP3D-r: 40 cycli at 92° C. 30", 60° C. 30" and 72° C. 60" resulting in BAC52, 1c06e11 harbouring SP3Dpen (FIG. 1).

BAC51, 1c06e11 was subsequently double digested with BamHI/SpeI and ligated in pUC 18 XbaI/BamHI double digest to create sub clones. Subsequently, sub clones were screened with SP3D-f2/SP3D-r marker to identify the individual clone harbouring SP3Dpen. Clone KEZ504 has been sequenced and it contained the complete SP3D gene/locus from *S. pennelii*, designated as SP3Dpen, SEQ ID NO: 6. (FIG. 2). Comparison of *S. lycopersicum* SP3D cDNA, accession number AY186735, with the *S. pennellii* SP3D cDNA revealed that SP3Dpen had 4 nucleotide changes. Two single nucleotide polymorphisms (SNP) are located in the first exon on position 15 (T=>C) and 120 (C=>T), the third SNP is in the second exon on position 270 (C=>T) and the fourth SNP is positioned in the fourth exon, on position 387 (G=>A), see FIG. 3. All these SNPs were synonymous. It was therefore concluded that the property of spi=2 was not caused by the gene itself but due to regulation of the gene.

Example 2

Causal SNP in Promoter, Wild Relatives

One of the determination keys of *Solanum* species is sympodial index. Species with two leaves between trusses (spi=2) are *Solanum neorickii, Solanum chmielewskii, Solanum chilense, Solanum peruvianum*, and *Solanum pennellii*. Species with three leaves between trusses (spi=3) are *S. habrochaites, S. cheesmaniae, S. pimpinellifolium* and *S. lycopersicum*.

To verify the hypothesis that spi=2 is caused by a change upstream of the gene several wild relatives have been studied. Fifty-three wild relatives of the mentioned species were re-sequenced using primers SP3D-10fa and dSP3D-r1. Of the group of 53 wild relatives, 11 represented *S. cheesmaniae*, 2 represented *S. chilense*, 7 represented *S. habrochaites*, 10 represented *S. neorickii*, 1 represented *S. pennellii*, 7 represented *S. peruvianum*, 11 represented *S. chmielewskii*, 1 represented *S. lycopersicum*, and 3 represented *S. pimpinellifolium*.

Figure 5:
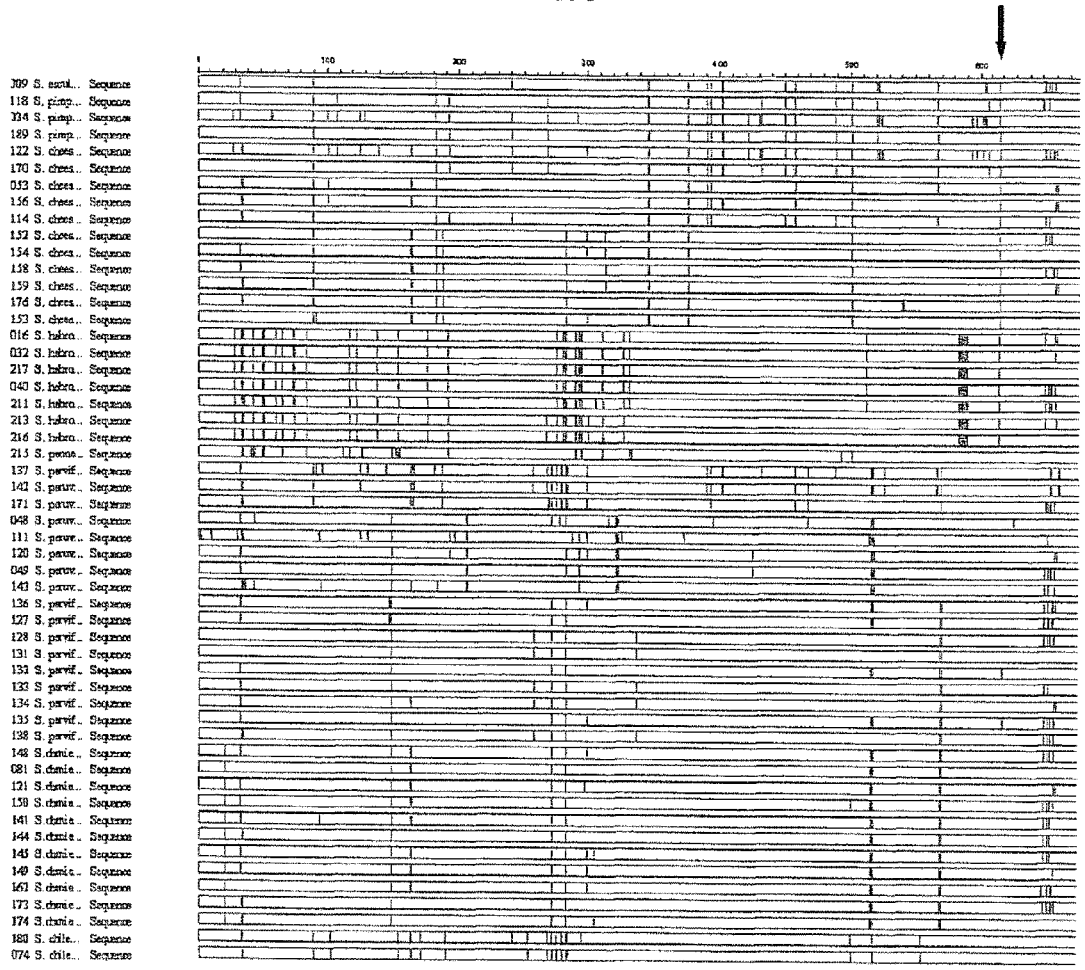
FIG. 5 shows the DNA sequence alignment of the SP3Dpen promoter region 1251-1874 with other wild relatives of the Solanaceae family, indicating that polymorphisms upstream and downstream of the CA motif are not linked to the properties of spi=2 or spi=3. Grey bars indicate a <49% match.

Sequence comparisons revealed a CA motif 62-61 nucleotides upstream of gene initiation in all spi=2 relatives whereas spi=3 species exhibit a CT or TA nucleotide motif, see FIG. 4. Moreover, polymorphisms upstream and downstream of the CA motif where not linked with sympodial index (see FIG. 5).

Example 3

Phenotypes of F1 Hybrids with and without SP3Dpen

Introgression line 49015-2 harbouring the SP3Dpen from *S. pennellii* la716 has been crossed with Enza Zaden *S. lyco-*

Figure 6:
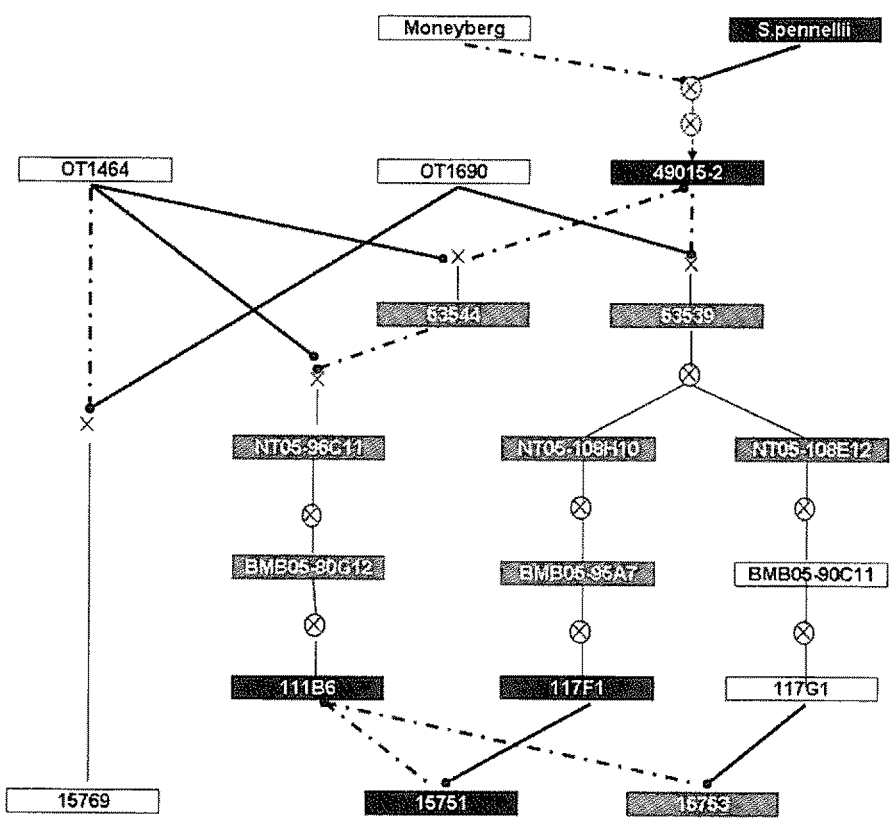
FIG. 6 is a breeding scheme of a F1 hybrid with and without SP3Dgene. Names in black boxes are SP3Dpen, white boxes are SP3Desc and grey boxes are heterozygous.

*persicum* lines OT1464 and OT1690. The resulting F1 hybrids have been backcrossed with OT1464 or selfed in the case of the OT1690 cross. Plants with SP3Dpen were selected with dCAPS marker dSP3D-1fr; primers dSP3D-f/dSP3D-r, PCR conditions 40 cycli at 92° C. 30", 55° C. 60" and 72° C. 60", digested by HpyCH4V, separated on 3% ms-8 agarose (Hispanagar). Besides the dSP3D-1fr marker, marker assisted backcross has been used to identify the highest recurrent parent, as known for those who are skilled in the art, resulting in plant NT05-96e11 for the OT1464 background and NT05-108h10 and NT05-108e12 for the OT1690 background. These individual plants were 2 times selfed, selected again with dSP3D marker and by marker assisted backcross, resulting in plants 111B6 for the OT1464 background and plants 117F1 and 117G1 for the OT1690 background. Thereafter F1 hybrids where made by crossing 111B6×111F1 resulting in 15751 (homozygous SP3Dpen), 111B6×117G1 resulting in 15753 (heterozygous) and OT1690×OT1464 resulting in 15769 as the SP3Desc homozygous control, see FIG. 6.

Four plants per hybrid were grown in the greenhouse during June 2006—end October 2006 under normal growing practice and evaluated for sympodial index by counting the number of leaves between successive trusses, number of leaves till first truss, average fruit weight, yield, number of fruit and trusses. The average sympodial index was 2.4 for SP3Dpen, 2.5 for heterozygous plants and 2.7 for SP3Desc (FIG. 7). As expected the number of leaves till first truss has changed and decreased from 7.5 for Sp3Desc to 5.8 for Sp3Dpen and heterozygous hybrids. The average fruit weight was similar between hybrids ranging from 57 till 59 g/fruit. As expected the number of trusses increased, 9 for SP3Desc to 14 for SP3Dpen. The number of fruit per truss increased from 6.7 for SP3Desc to 7.6 for SP3Dpen. This adds roughly 0.7 kg to the total yield of homozygous SP3Dpen F1 hybrids during this growth period.

These data reveal that the total yield improvement observed after 5 months in the plants comprising the promotor sequence of the invention as compared to plants not comprising said promotor sequence, is due to an increased number of trusses and in the case of homozygous SP3Dpen also to an increased number of fruits per truss. As a result, the total yield of 4 plants per hybrid is improved from 3.5 kg to 5.0 kg and 6.0 kg for SP3Desc, SP3Desc/pen and SP3Dpen respectively.

The yield improvement by SP3Dpen is due to the promotor sequence of SP3Dpen, comprising the CA motif 62-61 nucleotides upstream of start of the gene.

---

We claim:

1. A plant comprising in its genome a heterologous promotor sequence having a nucleotide sequence having at least 95% identity with SEQ ID NO: 31, capable of directing transcription of a downstream gene that is operably linked to said promotor sequence, wherein the promotor sequence is derived from a species of the Solanaceae family having a sympodial index of 2, for reducing sympodial index in plants having a sympodial index of 3 or more,
   wherein said promotor sequence comprises a CA motif at positions 19-20 of SEQ ID NO: 31,
   wherein said promotor sequence is derived from a species of the Solanaceae family, selected from the group consisting of S. pennellii, S. neorickii, S. chmielewskii, S. chilense, and S. peruvianum, and
   wherein said plant is selected from the group consisting of S. habrochaites, S. cheesmaniae, S. pimpinellifolium and S. lycopersicum.

2. The plant according to claim 1, wherein the promotor sequence is derived from S. pennellii and consists of the nucleotide sequence of nucleotides 1251-1874 of SEQ ID NO: 6.

3. A gene construct comprising a promotor sequence having at least 95% identity with SEQ ID NO: 31, said promotor sequence comprising a CA motif at positions 19-20 of SEQ ID NO: 31 and said promotor sequence being operably linked to a heterologous cDNA sequence having at least 75% identity with SEQ ID NO: 7.

4. The gene construct according to claim 3, wherein the cDNA sequence comprises a nucleotide sequence having at least 85% identity with the cDNA sequence of SEQ ID NO: 7.

5. The gene construct according to claim 4, wherein the cDNA sequence comprises a nucleotide sequence having at least 90% identity with the cDNA sequence of SEQ ID NO: 7.

6. The gene construct according to claim 5, wherein the cDNA sequence comprises a nucleotide sequence having at least 95% identity with the cDNA sequence of SEQ ID NO: 7.

7. The gene construct according to claim 6, wherein the cDNA sequence comprises a nucleotide sequence having at least 99% identity with the cDNA sequence of SEQ ID NO: 7.

8. The gene construct according to claim 3, wherein the cDNA sequence consists of the nucleotide sequence of SEQ ID NO: 7.

9. A method for providing plants of the Solanaceae family having a reduced sympodial index comprising introducing into the genome of said plants a heterologous promotor sequence having a nucleotide sequence having at least 95% identity with SEQ ID NO: 31, capable of directing transcription of a downstream gene that is operably linked to said promotor sequence, wherein the promoter sequence is derived from a species of the Solanaceae family having a sympodial index of 2, wherein the promotor sequence comprises a CA motif at positions 19-20 of SEQ ID NO: 31, wherein said promotor sequence is derived from a species of the Solanaceae family, selected from the group consisting of *S. pennellii, S. neorickii, S. chmielewskii, S. chilense*, and *S. peruvianum*, and wherein said plant is selected from the group consisting of *S. habrochaites, S. cheesmaniae, S. pimpinellifolium* and *S. lycopersicum*.

10. The method according to claim 9, wherein the sympodial index is reduced to a sympodial index of 2.

11. A method for increasing crop yield in a plant of the Solanaceae family having a sympodial index of 3 or more, comprising introducing into the genome of said plant a heterologous promoter sequence having a nucleotide sequence having at least 95% identity with SEQ ID NO: 31, capable of directing transcription of a downstream heterologous gene that is operably linked to said promoter sequence, wherein the promoter sequence is derived from a species of the Solanaceae family having a sympodial index of 2, in operable linkage with a downstream SP3D gene, wherein the promotor sequence comprises a CA motif at positions 19-20 of SEQ ID NO: 31, wherein said promotor sequence is derived from a species of the Solanaceae family, selected from the group consisting of *S. pennellii, S. neorickii, S. chmielewskii, S. chilense*, and *S. peruvianum*, and wherein said plant is selected from the group consisting of *S. habrochaites, S. cheesmaniae, S. pimpinellifolium* and *S. lycopersicum*.

12. The method according to claim 9, wherein the plant is *S. lycopersicum*.

13. A plant, obtained by the method according to claim 9, wherein the plant has in its genome a promotor sequence having a nucleotide sequence having at least 95% identity with SEQ ID NO: 31, and wherein the promoter sequence comprises a CA motif at positions 19-20 of SEQ ID NO: 31.

14. Seed and/or other plant parts derived from a plant according to claim 13, wherein the seed and/or other plant parts comprise in their genome a heterologous promoter sequence having a nucleotide sequence having at least 95% identity with SEQ ID NO: 31, said promoter sequence comprising a CA motif at positions 19-20 of SEQ ID NO: 31.

15. The method according to claim 11, wherein the plant is *S. lycopersicum*.

16. A plant, obtained by the method according to claim 11, wherein the plant has in its genome a promotor sequence having a nucleotide sequence having at least 95% identity with SEQ ID NO: 31, and wherein the promoter sequence comprises a CA motif at positions 19-20 of SEQ ID NO: 31.

17. Seed and/or other plant parts derived from a plant according to claim 16, wherein the seed and/or other plant parts comprise in their genome a heterologous promoter sequence having a nucleotide sequence having at least 95% identity with SEQ ID NO: 31, said promoter sequence comprising a CA motif at positions 19-20 of SEQ ID NO: 31.

\* \* \* \* \*